United States Patent [19]

Garbuny et al.

[11] 4,147,602
[45] Apr. 3, 1979

[54] PRODUCTION OF HYDROGEN AND CARBON DIOXIDE

[75] Inventors: Max Garbuny, Churchill Borough; D. Colin Phillips, Monroeville, both of Pa.

[73] Assignee: Westinghouse Electric Corp., Pittsburgh, Pa.

[21] Appl. No.: 881,349

[22] Filed: Feb. 27, 1978

[51] Int. Cl.$^2$ ............................................. B01J 1/10
[52] U.S. Cl. .......................... 204/157.1 R; 204/158 R; 250/527; 204/DIG. 11
[58] Field of Search ................ 204/DIG. 11, 157.1 R, 204/158 R

[56] References Cited

FOREIGN PATENT DOCUMENTS 1443948  4/1969  Fed. Rep. of Germany .... 204/157.1 R
142637   4/1961  U.S.S.R. .......................... 204/157.1 R

OTHER PUBLICATIONS

Ellis et al, The Chem. Action of Ultraviolet Rays (1941) pp. 416, 417, 868.

Primary Examiner—Howard S. Williams
Attorney, Agent, or Firm—R. D. Fuerle

[57] ABSTRACT

Hydrogen and carbon dioxide are produced by activating a mixture of carbon monoxide and water with monochromatic light. Preferably, a unidirectional stream of steam activated with a laser at 5400 cm.$^{-1}$ collides with a carbon monoxide stream to effect the reaction. The carbon dioxide can then be reacted with water to produce formaldehyde. Ketene and water are produced by exposing the formaldehyde to ultraviolet light.

7 Claims, 1 Drawing Figure

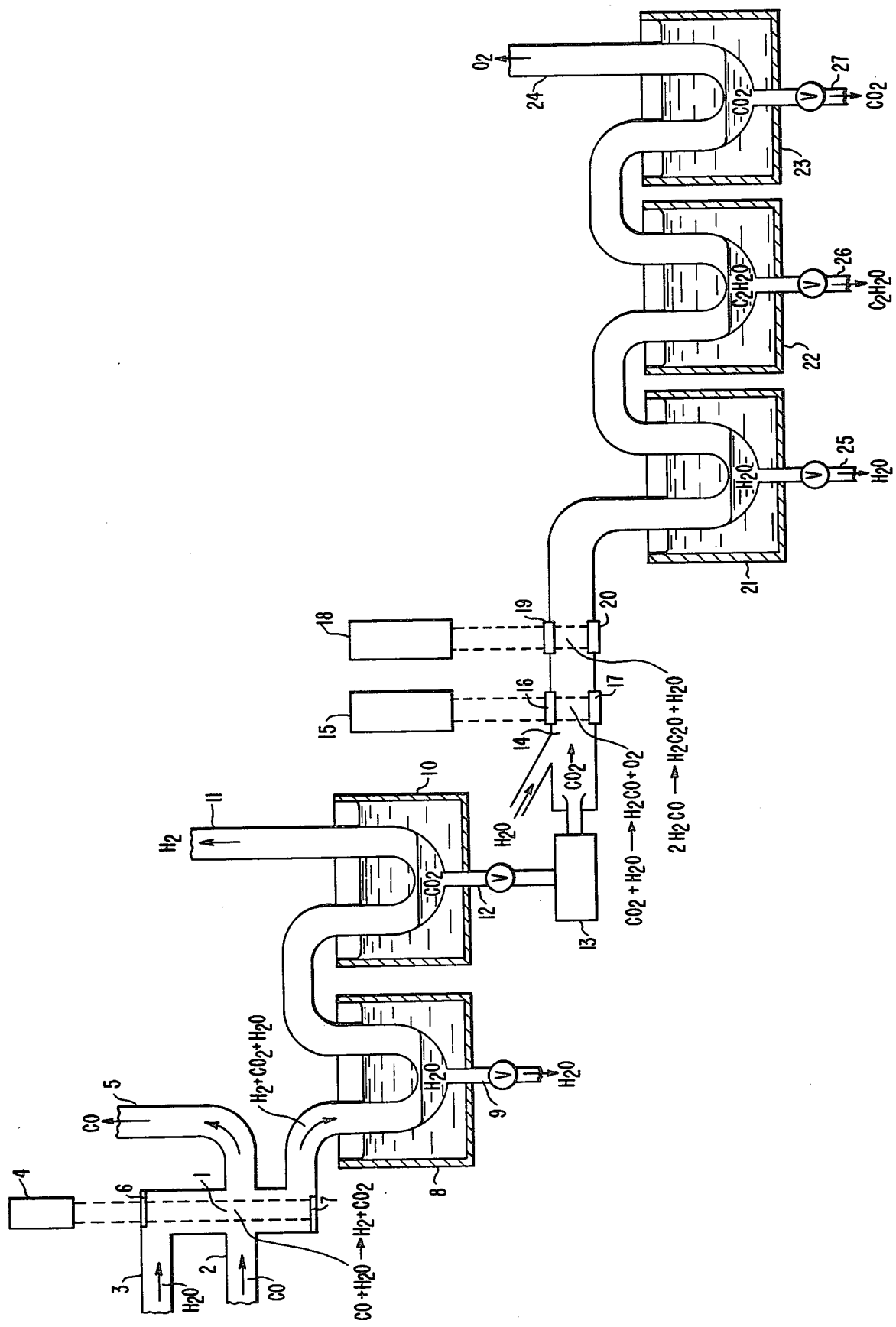

PRODUCTION OF HYDROGEN AND CARBON DIOXIDE

BACKGROUND OF THE INVENTION

Carbon dioxide and carbon monoxide are present in only small quantities in the air, but often form a large part of the gas effluent of various industrial processes. A process for converting carbon dioxide and water to formaldehyde using a laser is disclosed in application Ser. No. 599,494 filed July 28, 1975. Although carbon dioxide is not considered to be a pollutant, that process does enable the off-hour electrical generating capacity of utilities to be used to produce a useful chemical from extremely inexpensive materials.

Carbon monoxide, on the other hand, is a pollutant which must be removed from effluent gases. It therefore has a "negative cost" and a process which could not only remove it but could produce a useful chemical as well would be doubly useful.

SUMMARY OF THE INVENTION

We have found that carbon monoxide and water will react to produce hydrogen and carbon dioxide when activated with monochromatic light. We have also found that formaldehyde can be dissociated into ketene and water by exposure to ultraviolet light. Thus, one may start with water and carbon monoxide and, using the carbon dioxide water reaction to produce formaldehyde disclosed in application Ser. No. 599,494 filed July 28, 1975, produce ketene and hydrogen. A pollutant, carbon monoxide can thereby be converted into a useful fuel, hydrogen, and a useful organic chemical, ketene, from which many other compounds can be synthesized.

DESCRIPTION OF THE INVENTION

The FIGURE is a diagram illustrating the three-step process of this invention. In the FIGURE carbon monoxide and water enter reaction chamber 1 from conduits 2 and 3 respectively where they are exposed to monochromatic light from laser 4 resulting in their reaction according to the equation $CO+H_2O \rightarrow CO_2+H_2$. The unreacted carbon monoxide and any other unreactive gases that may also be present pass through exhaust port 53. The unreacted carbon monoxide may be recycled if it is present in sufficient quantities. Both the carbon monoxide and the water are in the fluid state (i.e., gases or liquids) and gases are preferred because they present effective absorption of monochromatic light by resonance, and because the gaseous state allows the excited molecular state to preserve the excitation to a large extent until a chemically reactive collision occurs. The reaction may also be performed on a static mixture of carbon monoxide and water but a dynamic process is preferred as it can continuously handle large quanities of reactants. In a dynamic process the reactant to be activated by the light moves with a forward component of velocity at least 10 times its lateral component of velocity. This condition is preferably obtained at supersonic speeds. Details on the dynamic process can be found in application Ser. No. 599,494, filed July 28, 1975, herein incorporated by reference. The temperature of the mixture is preferably about 20 to about 100° C. for the most efficient reaction. Either the water or the carbon monoxide may be activated by the laser. The carbon monoxide is preferably activated at a wavelength of about 5400 cm.$^{-1}$. Preferably, the water is activated because the carbon monoxide was found to be less reactive. Water can be activated at a wavelength of about 5400 cm.$^{-1}$. The laser excites vibrational states in the molecules to induce their reaction, but it does not ionize them (i.e., knock off electrons). The laser light passes through window 14 and is reflected off mirror 7 to increase its effectiveness.

Unreacted water and the carbon dioxide and hydrogen formed by the reaction, pass into condenser 8 which lowers the temperature below 100° C. causing the water to condense out. It can be removed through drain 9. The remaining carbon dioxide and hydrogen enter a second condenser 10 which cools the carbon dioxide. The hydrogen then passes out exhaust port 11.

The carbon dioxide passes through conduit 12 into pump 13 where it is preferably accelerated as a gas to supersonic velocities into reaction chamber 14. Water, also preferably as a gas, is injected into the reaction chamber. Light from laser 15 passes through window 16 into the reaction chamber and reflects off mirror 17. The carbon dioxide and water react to produce formaldehyde and oxygen according to the equation $CO_2+H_2O \rightarrow H_2CO+O_2$. The light may activate either the water or the carbon dioxide. Water can be activated at a wavelength of about 5400 cm.$^{-1}$ and carbon dioxide can be activated at a wavelength of about 2350 cm.$^{-1}$. A more complete description of this reaction can be found in application Ser. No. 599,494, filed July 28, 1975, herein incorporated by reference.

The formaldehyde that is formed continues down the reaction chamber where is encounters ultaviolet light from ultraviolet light source 18 which dissociates it into ketene and water according to the equation $2CH_2O \rightarrow C_2H_2O +H_2O$. Once again, a window 19 and a mirror 20 are used to permit the light to enter the chamber and increase its effectiveness. This reaction is preferably conducted at about 20 to about 200° C. for best results. The oxygen, the unreacted water and carbon dioxide, and the ketene product pass into condenser 21 which cools the mixture below 100° C. condensing out the water. The remaining ketene, oxygen, and carbon dioxide pass into condenser 22 which cools the mixture between $-56°$ and $-78°$ C. condensing out the ketene. The remaining carbon dioxide and oxygen pass into condenser 23 which liquefies the carbon dioxide, which can be recycled if desired. The oxygen leaves through conduit 24. Other methods of separation may also be used. The water condensers 8 and 21 and the carbon dioxide condensers 10 and 23 may be combined or single coolant used for all the condensers, as is known in the art. The water, ketene, and carbon dioxide are released through conduits 25, 26, and 27 respectively.

Ketene readily photodecomposes into methylene diradical and carbon monoxide at a wavelength of 3800 to 2400 Å or by thermal decomposition according to the equation $C_2H_2O \rightarrow \cdot CH_2 + CO$. The methylene diradical is one of the most reactive organic radicals known and is extremely versatile in synthesizing other compounds. The following are a few of its many reactions:

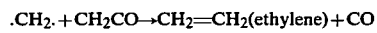

$\cdot CH_2 + CH_2CO \rightarrow CH_2=CH_2 (\text{ethylene}) + CO$

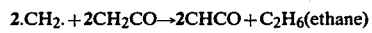

$2\cdot CH_2 + 2CH_2CO \rightarrow 2CHCO + C_2H_6 (\text{ethane})$

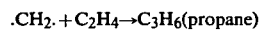

$\cdot CH_2 + C_2H_4 \rightarrow C_3H_6 (\text{propane})$

The following example further illustrates this invention.

EXAMPLE

A stagnant mixture of carbon monoxide and excess water was placed in a 30 cm. reaction tube at a pressure of 100 Torr. Light from a 10 microwatt parametric tunable laser tuned to 5400 cm.$^{-1}$ was directed lengthwise through the tube for 60 hours.

Connected to the reaction tube was a small heated tube containing a 90% palladium-10% silver alloy which is semi-permeable to hydrogen but not to carbon monoxide. About 1 Torr of hydrogen was measured on the other side of the tube, indicating that the reaction $CO + H_2O \rightarrow CO_2 + H_2$ had occurred in the reaction tube.

We claim:

1. A method of reacting carbon monoxide and water to produce carbon dioxide and hydrogen comprising, in either order,
   (1) activating said carbon monoxide or said water with monochromatic light to form an activated specie and an unactivated specie;
   (2) bringing said activated specie and said unactivated specie into contact.

2. A method according to claim 1 wherein said species are gases.

3. A method according to claim 1 wherein the temperature of said water and carbon monoxide at the point of contact is about 20° to about 100° C.

4. A method according to claim 1 wherein the source of said light is a single longitudinal mode laser.

5. A method according to claim 1 wherein said activated specie is water and said light has a wavelength of about 5400 cm.$^{-1}$.

6. A method according to claim 5 wherein said water moves relative to said light in a unidirectional stream with a forward component of velocity at least ten times the lateral component of velocity, and said stream of water is activated before contacting carbon monoxide.

7. A method according to claim 6 wherein said carbon monoxide is moving in a gaseous stream.

* * * * *